(12) United States Patent
Frigg et al.

(10) Patent No.: US 8,454,606 B2
(45) Date of Patent: Jun. 4, 2013

(54) DEVICE FOR THE TREATMENT OF FRACTURES OF THE FEMUR

(75) Inventors: Robert Frigg, Bettlach (CH); Eric Hattler, Solothurn (CH); Walter Widmer, Oberdorf (CH); Elena Barrios, Port (CH)

(73) Assignee: Synthes USA, LLC, West Chester, PA (US)

( * ) Notice: Subject to any disclaimer, the term of this patent is extended or adjusted under 35 U.S.C. 154(b) by 1625 days.

(21) Appl. No.: 10/532,909

(22) PCT Filed: Oct. 29, 2002

(86) PCT No.: PCT/CH02/00584
§ 371 (c)(1),
(2), (4) Date: Dec. 16, 2005

(87) PCT Pub. No.: WO2004/039270
PCT Pub. Date: May 13, 2004

(65) Prior Publication Data
US 2006/0149247 A1 Jul. 6, 2006

(51) Int. Cl.
*A61B 17/58* (2006.01)
(52) U.S. Cl.
USPC .......................................... 606/64
(58) Field of Classification Search
USPC ................. 606/62, 63, 64, 65, 66, 67, 68
See application file for complete search history.

(56) References Cited

U.S. PATENT DOCUMENTS

| | | | |
|---|---|---|---|
| 4,432,358 A * | 2/1984 | Fixel | 606/66 |
| 5,032,125 A * | 7/1991 | Durham et al. | 606/62 |
| 5,324,292 A | 6/1994 | Meyers | |
| 5,454,813 A | 10/1995 | Lawes | |
| 5,531,748 A * | 7/1996 | de la Caffiniere | 606/62 |
| 5,908,422 A * | 6/1999 | Bresina | 606/67 |
| 6,187,007 B1 * | 2/2001 | Frigg et al. | 606/72 |
| 6,648,889 B2 * | 11/2003 | Bramlet et al. | 606/62 |
| 2003/0074000 A1 * | 4/2003 | Roth et al. | 606/62 |
| 2004/0044345 A1 * | 3/2004 | DeMoss et al. | 606/73 |
| 2005/0010223 A1 * | 1/2005 | Gotfried | 606/62 |
| 2006/0155281 A1 * | 7/2006 | Kaup et al. | 606/65 |

FOREIGN PATENT DOCUMENTS

| | | |
|---|---|---|
| DE | 1 071 285 | 6/1960 |
| DE | 197 23 339 A1 | 12/1998 |
| EP | 0 441 577 A3 | 8/1991 |

* cited by examiner

*Primary Examiner* — Nicholas Woodall
(74) *Attorney, Agent, or Firm* — Fay Kaplun & Marcin, LLP

(57) ABSTRACT

A device for treating fractures of the femur and includes an intra-medullary pin (1) with a central longitudinal axis (2), a front piece (3), which is introduced into the medullary channel of the femur, a rear piece (4) and a hole (5) going through the rear piece (4) at an angle to the longitudinal axis (2) with a non-circular cross-section (6). A sliding sleeve (10) that is introduced through the hole (5) with non-circular cross-section, has a front end (11), a rear end (12), a central longitudinal drilling (13), an outer sleeve surface (14), an inner sleeve surface (15) and a longitudinal axis (16). A longitudinal bone fixation element (20) with a longitudinal axis (21), a head piece (22) with fixation element (23), which is brought into engagement with the femur head on use and a shaft (24), which is introduced co-axially into the sliding sleeve (10), whereby the outer sleeve surface (14) of the sliding sleeve (10) has a non-circular cross-section (17), at least in a partial region. The inner sleeve surface (5) of the sliding sleeve (10) has a round cross-section (18) and fixation elements (30) are provided for the selective blocking of the rotation of the longitudinal bone fixation element (20) in the sliding sleeve (10).

22 Claims, 5 Drawing Sheets

DEVICE FOR THE TREATMENT OF FRACTURES OF THE FEMUR

RELATED APPLICATION DATA

This application is the United States National Stage Application of International Application No. PCT/CH02/00584, filed Oct. 29, 2002.

FIELD OF THE INVENTION

The present invention concerns a device for the treatment of fractures of the femur, and, more particularly, to a device including an intramedullary pin, a longitudinal bone fixation element configured to engage the femoral head, a sliding sleeve, and a locking mechanism configured to selectively lock rotation of the bone fixation element relative to both the sleeve and the pin when in a first position and permit free rotation of the bone fixation element relative to both the sleeve and the pin when in a second position.

BACKGROUND OF THE INVENTION

Devices, whereby a securing of the femoral head against rotation is attempted by a single hip screw, i.e. a longitudinal bone fixing means, are already known. A device is known, for example, from EP-B 0 441 577, that has a sleeve accommodating the hip screw in a sliding manner, while the sleeve can be secured against rotation in the intramedullary pin by a locking screw proximally introduced into the intramedullary pin. The shaft of the hip screw and the bore of the sleeve are, however, not circular, so that the hip screw cannot rotate in the sleeve. However, during the introduction into the head of the femur the hip screw has to be able to rotate. For this reason during implantation the hip screw has to be inserted first and the sliding sleeve only afterwards. The two elements cannot be introduced together, so that the operation will be a complicated one. There is further the danger, that the hip screw would move medially when a compression screw is not additionally employed. A further disadvantage is, that the locking screw has to introduced from above (cranially) into the intramedullary pin, representing a further operating procedure. Finally, in the case of a potential subsequent removal of the hip screw, a relatively substantial intervention is required to release the locking screw, screwed proximally into the intramedullary pin, in a step prior to removing the hip screw.

Furthermore, from U.S. Pat. No. 5,454,813 Lawes, an intramedullary pin with a hip screw and a sliding sleeve is known, wherein the transition in the intramedullary pin, the external and internal section of the sliding sleeve and the shaft of the hip screw have a non-circular construction. Consequently, the sliding sleeve acts as an anti-rotational means between the hip screw and the intramedullary pin. This known device has the same disadvantages as EP-B 0 441 577, i.e. a complicated operating technique, both during the implanting and removal of the hip screw and the medial movement can be prevented only with an additional component (tension adjuster).

The purpose of the preceding discussion of the state-of-the-art is merely to explain the field of the invention and does not mean that the state-of-the-art quoted has actually been published or is public knowledge at the time of this application.

This is where the invention wants to provide remedy. The invention is based on the problem to produce a device for the treatment of femoral fractures, particularly of proximal femoral fractures, that allows a simple and reliable blocking of the rotation between the longitudinal bone fixing element (e.g. a hip screw) and the intramedullary pin, simplifies and shortens the operating procedure and does not limit the lateral sliding of the longitudinal bone fixing element.

SUMMARY OF THE INVENTION

The invention achieves the objective set by a device having an intramedullary pin, a longitudinal bone fixation element configured to engage the femoral head, a sliding sleeve, and a locking mechanism configured to selectively lock rotation of the bone fixation element relative to both the sleeve and the pin when in a first position and permit free rotation of the bone fixation element relative to both the sleeve and the pin when in a second position.

With the device according to the invention the advantage is achieved, that the front portion of the longitudinal bone fixing element, preferably constructed as a screw or a helical blade, can be optimally anchored in the spongiosa of the femoral head, because the shaft of the longitudinal bone fixing element remains rotationally freely displaceable in the surrounding sliding sleeve, and at the same time the sliding sleeve, with the longitudinal bone fixing element accommodated in it, remains axially freely displaceable.

So that the clinical manipulation of this combination of longitudinal bone fixing element and sliding sleeve remains simple, preferably both elements can be so pre-assembled, that while the longitudinal bone fixing element can freely rotate in the sliding sleeve, it is axially fixed relative to it. The advantage of this pre-assembled construction is that when the longitudinal bone fixing element is introduced into the femoral head, it does not need to be specially aligned and when driven in it can rotate helically in the femoral head. At this stage the longitudinal bone fixing element is not yet secured against rotation. Thus the surgeon can rotationally correct the femoral head before he blocks the rotation of the longitudinal bone fixing element in the bore of the shaft of the longitudinal bone fixing element by screwing in the fixing screw from the side.

In a preferred development at the free end of the shaft of the longitudinal bone fixing element a bore, that preferably has an inside thread, is provided coaxially with the longitudinal axis.

In the case of a special embodiment the locking means comprise a fixing screw with a screw head with a diameter of D and a screw shank with a diameter of d with an outside thread, while D>d. At the same time the outside thread of the screw shank corresponds to the inside thread of the bore of the shaft of the longitudinal bone fixing element and can be screwed into its bore until the screw head abuts against the rear end of the sliding sleeve and by a further tightening of the fixing screw, acting as locking means, a force-locked connection will result between the longitudinal bone fixing element and the sliding sleeve.

In a further embodiment the shaft of the longitudinal bone fixing element can rotate but is locked in the sliding sleeve in the axial direction. For this purpose the shaft of the longitudinal bone fixing element may have a first annular groove and the internal jacket surface of the sliding sleeve a second annular groove. Furthermore an element, blocking the axial displacement of the shaft in the sliding sleeve, is provided preferably in the form of a ring, engaging both annular grooves. However, instead of the ring other blocking elements (for example in the form of a pin) may be used.

In another embodiment the rear end of the sliding sleeve protrudes past the free end of the shaft of the longitudinal bone fixing element by a specific amount x, preferably by at least 0.01 mm.

In the case of another special embodiment instead of an inside thread an outside thread is provided on the free end of the shaft. In the case of this embodiment instead of a fixing screw the locking means is a nut, with an inside thread that corresponds to the outside thread of the shaft.

In the case of special embodiment the non-circular cross-section of the passage of the intramedullary pin can have peripheral part-sections in the form of partial circular arcs. This combination of a non-circular cross-section with a round one allows on the one hand the use of an intramedullary pin constructed in this manner with the non-circular sliding sleeve according to the invention on the other, but also without a sliding sleeve, merely with a longitudinal bone fixing element (e.g. a hip screw), that has a round shaft, wherein due to this construction a good guiding of the round shaft of the bone fixing element (e.g. a hip screw) will be achieved despite the non-circular passage. Thus, provided it has a second transverse bore, the intramedullary pin constructed in this manner can be used also in a conventional manner with two bone fixing elements (e.g. two hip screws).

The fixing means of the longitudinal bone fixing element is preferably a helical blade, preferably a double helical blade. However, the fixing means can be also a screw thread with a relatively fine pitch, a chisel, a pin, a T-section or a double T-section.

In the case of a particularly special embodiment the head portion of the longitudinal bone fixing element is constructed as a multi-start thread, preferably as a four-start thread. By virtue of this configuration the positioning of the bone fixing element is of no consequence, unlike in the case of a single-start thread. At the same time the thread of the head portion can have a pitch of at least 50 mm, preferably at least 80 mm. The advantage of this relatively coarse pitch is the higher resistance against the rotation of the bone fixing element. In addition, the bone fixing element, constructed as a helical blade, causes less damage to the bony substance than a conventional hip screw with a relatively fine pitch thread. The bone is compacted rather than cut by the helical surfaces of the helical blade.

The locking means, that can be realised in the form of a fixing screw or a nut, are preferably so dimensioned, that they act as an axial stop with regard to the passage of the intramedullary pin. This stop prevents a too wide a medial movement of the bone fixing element.

BRIEF DESCRIPTION OF THE DRAWINGS

The invention and developments of the invention are explained in detail in the following based on partly schematic illustrations of several embodiments.

They show in.

DETAILED DESCRIPTION OF THE PREFERRED EMBODIMENTS

Figures 1, 2:
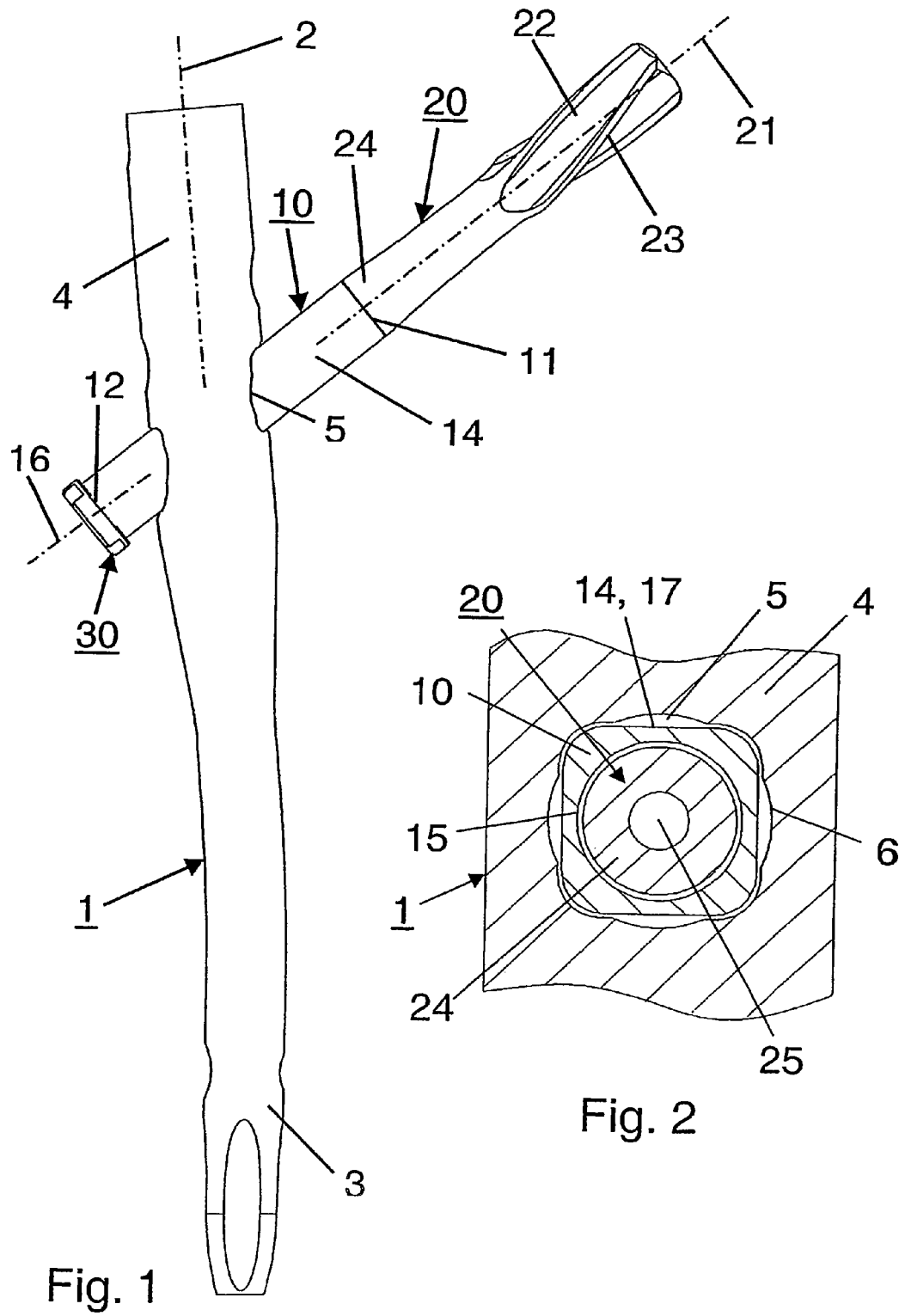
FIG. 1—a side view through the device according to the invention.
FIG. 2—a partial section through an intramedullary pin in the region of its oblique passing through with a longitudinal bone fixing element inserted and a sliding sleeve, FIG. 3—a partial section through a modified intramedullary pin in the region of its oblique passing through with a longitudinal bone fixing element inserted and a sliding sleeve, FIG. 4—a partial section through another modified intramedullary pin in the region of its oblique passing through with a longitudinal bone fixing element inserted and a sliding sleeve, FIG. 5—a partial longitudinal section through the device according to FIG. 1, FIG. 6—an enlarged detail of the circle VI of FIG. 5, FIG. 7—a section along the line VII-VII of FIG. 5, FIG. 8—a longitudinal section through a modified sliding sleeve with a helical blade pre-assembled therein, FIG. 9—a longitudinal section through a modification of the sliding sleeve according to FIG. 8 with a helical blade pre-assembled therein.

In FIGS. 1 to 2 as well as 5 to 7 a device for the treatment of femoral fractures is illustrated, that comprises an intramedullary pin 1, a sliding sleeve 10, a longitudinal bone fixing element 20 in the form of a helical blade and a locking means 30 in the form of a fixing screw.

The intramedullary pin 1 has a central longitudinal axis 2, a front portion 3 that can be introduced into the medullary canal, a rear portion 4, as well as a passage 5 with a non-circular cross-section 6 that passes through the rear portion 4 obliquely to the longitudinal axis 2.

The sliding sleeve 10, that can pass through the non-circular passage 5, has a front end 11, a rear end 12, a central longitudinal bore 13, an external jacket surface 14, an internal jacket surface 15, as well as a longitudinal axis 16.

The longitudinal bone fixing element 20 in the form of a helical blade has a longitudinal axis 21, a head portion 22 with fixing means 23 in the form of a multi-start thread with a relatively coarse pitch, that can engage the femoral head during use, as well as a shaft 24 that can be coaxially introduced into the sliding sleeve 10.

The external jacket surface 14 of the sliding sleeve 10 has a non-circular cross-section 17, while the internal jacket surface 15 of the sliding sleeve 10 has a circular cross-section 18. Finally, locking means 30 are provided in the form of a fixing screw to enable the optional blocking of the rotation of the longitudinal bone fixing element 20 in the sliding sleeve 10. At the free end 27 of the shaft 24 of the longitudinal bone fixing element 20 a bore 25 is provided coaxially with the longitudinal axis 21, the bore having an inside thread 26.

Figure 6:
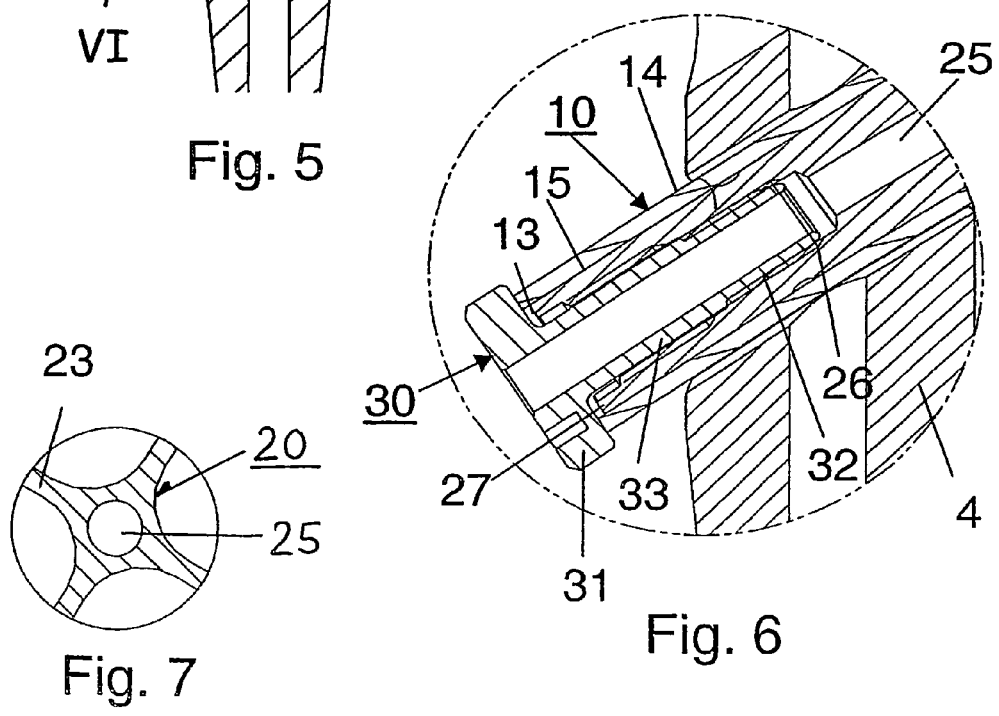

The locking means 30 in the form of a fixing screw has a screw head 31 with a diameter of D and a screw shank 33 with a diameter of d with an outside thread 32, while D>d (FIG. 6). The outside thread 32 of the screw shank 33 corresponds to the inside thread 26 of the bore 25 of the shaft 24 of the longitudinal bone fixing element 20 and can be screwed into the bore 25 until the screw head 31 abuts against the rear end 12 of the sliding sleeve 10 and a further tightening of the fixing screw, acting as locking means 30, will result in a force-locked connection between the longitudinal bone fixing element 20 and the sliding sleeve 10.

Figure 8:
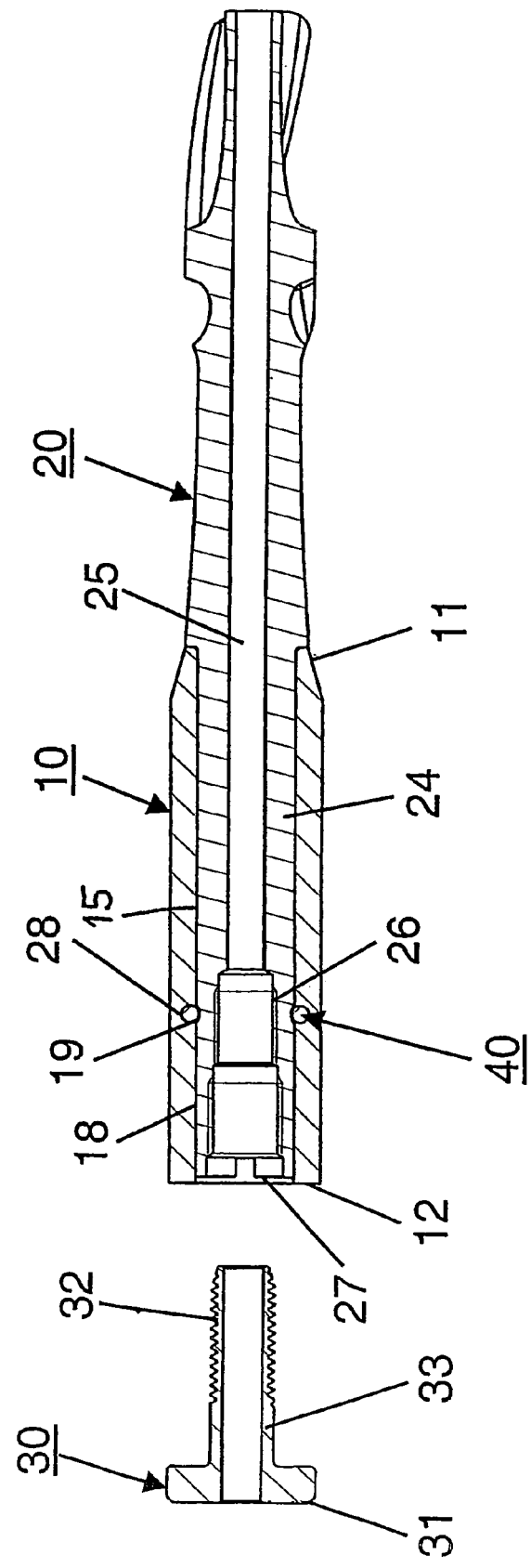

In the case of a further embodiment illustrated in FIG. 8 the shaft 24 of the longitudinal bone fixing element 20 has a first annular groove 28 and the internal jacket surface 15 of the sliding sleeve 10 a second annular groove 19. In these two annular grooves 28, 19 an element 40 is provided in the form of a ring, blocking the axial displacement of the shaft 24 in the sliding sleeve 10. By virtue of this the shaft 24 of the longitudinal bone fixing element 20 is mounted in a manner that allows rotation in the sliding sleeve 10 but locks it in the axial direction. At the same time the rear end 12 of the sliding sleeve 10 protrudes past the free end 27 of the shaft 24 of the longitudinal bone fixing element 20 by a specific amount x in order to ensure a reliable force-locking when the fixing screw is tightened. By virtue of this force locking it is possible to optionally block the rotation of the longitudinal bone fixing element 20 in the sliding sleeve.

FIG. 2 shows, how the cylindrical shaft 24 of the longitudinal bone fixing element 20, constructed as a hip screw, is mounted in a freely rotatable manner in the interior of the sliding sleeve 10, also with a cylindrical internal jacket surface 15. In contrast to that the external jacket surface 14 of the sliding sleeve 10, having an essentially square-shaped, i.e. non-circular, cross-section 17, is secured against rotation in the passage 5 of the intramedullary pin 1 also having a non-circular cross-section 6. As FIG. 2 illustrates, the non-circular cross-section 6 of the passage 5 has also an approximately square-shaped construction, but has additional peripheral part-sections in the form of partial circular arcs. Due to this construction the intramedullary pin 1 can be used also with a conventional hip screw with a cylindrical shaft, i.e. without a sleeve.

Figure 3:
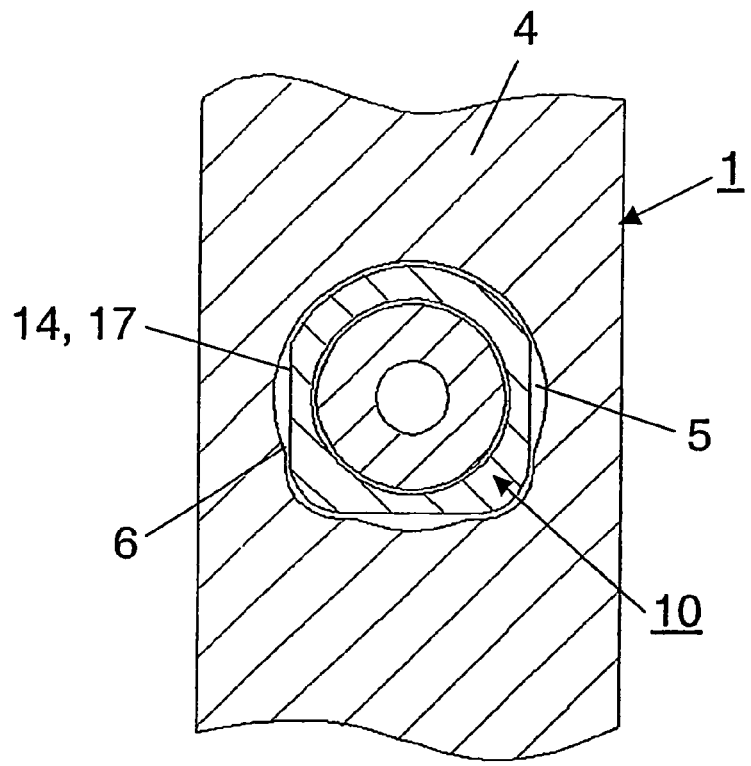

FIG. 3 illustrates a version of a non-circular cross-section 6 of the passage 5, wherein two small partial circular arcs and a larger partial circular arc are present. The non-circular cross-section 17 of the external jacket surface 14 of the sliding sleeve 10 is correspondingly constructed. In contrast to the execution according to FIG. 2 it will be simple to manipulate it because due to the symmetry an incorrect insertion of the hip screw is prevented.

Figure 4:
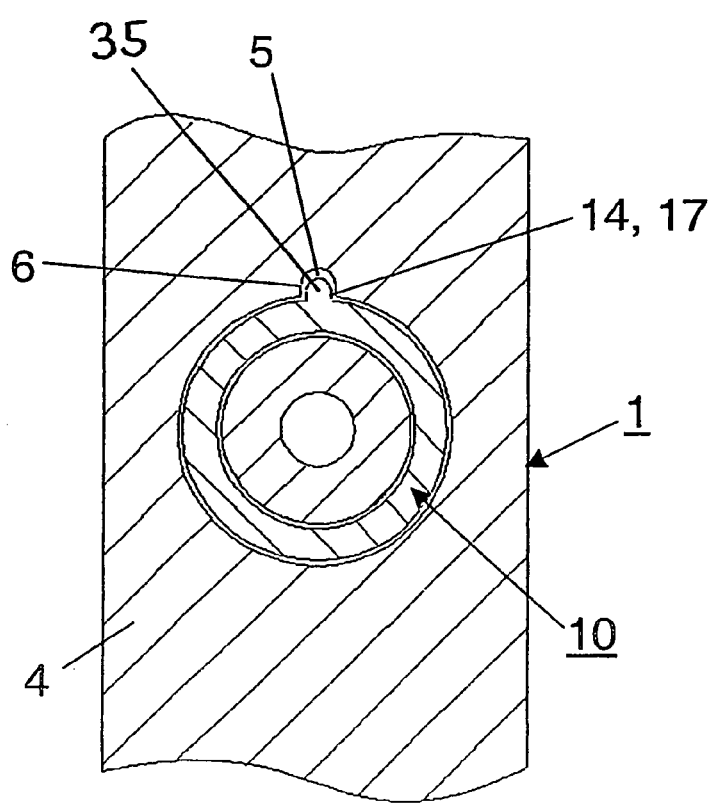

In FIG. 4 a further version of a non-circular cross-section 6 of the passage 5 is illustrated, wherein while the cross-section is essentially circular, it has a longitudinal slot, in which a longitudinal web 35 is accommodated in a form-locking manner on the external jacket surface 14 of the sliding sleeve 10, so that the rotation of both elements is assured.

Figure 5:
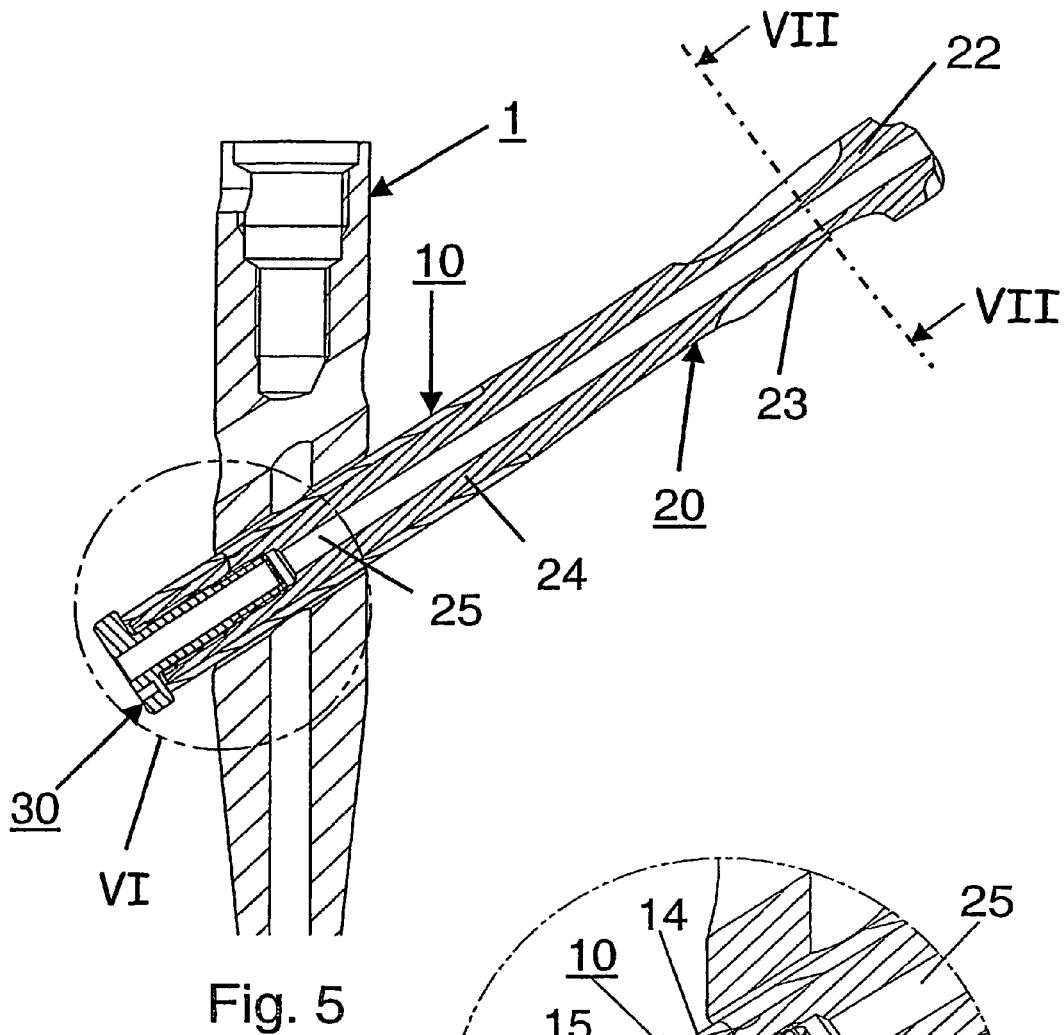
Figure 7:
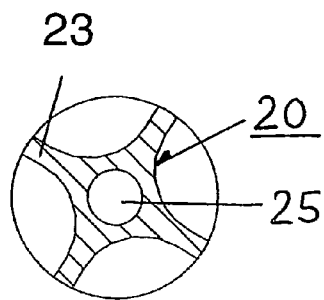

As FIG. 7 illustrates, the fixing means 23 of the longitudinal bone fixing element 20 according to FIG. 5 are constructed as a four-start helical blade, wherein the thread has a pitch of approx. 120 mm.

Figure 9:
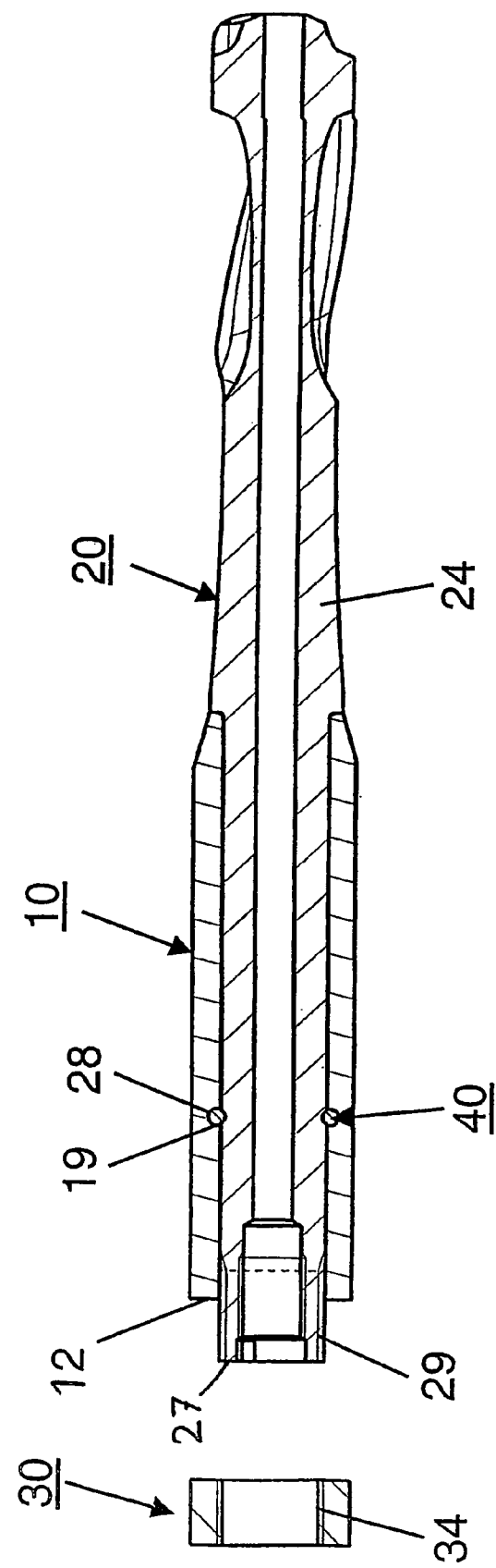

FIG. 9 illustrates a version of the device according to the invention, wherein instead of a fixing screw, acting as a locking means 30, a nut is provided. Accordingly, instead of an inside thread, the free end 27 of the shaft 24 of the longitudinal bone fixing element 20 has an outside thread 29, that corresponds with the inside thread 34 of the nut (locking means 30). The inside thread 34 and the outside thread 29 are round. At the same time the free end 27 of the shaft 24 of the longitudinal bone fixing element 20 protrudes past the rear end 12 of the sliding sleeve 10 by a specific amount x, so that the nut could be screwed on the outside thread 29. As soon as the nut abuts against the rear end 12 of the sliding sleeve 10, a reliable force-locking is established if the nut is further turned. By virtue of this force-locking it is possible to optionally block the rotation of the longitudinal bone fixing element 20 in the sliding sleeve 10.

The invention claimed is:

1. A device for the treatment of femoral fractures comprising:
an intramedullary pin having a first longitudinal axis, a proximal portion, a distal portion, and at least one transverse opening through the proximal portion of the pin, the at least one transverse opening forming an oblique angle with the first longitudinal axis and having a non-circular cross-section;
a bone fixation element having a second longitudinal axis, a first end, a second end, and a shaft, the first end configured and dimensioned to engage bone in the femoral head,
a sliding sleeve having a central bore, an interior surface profile, and an exterior surface profile, the central bore and interior surface profile configured to receive the shaft of the bone fixation element while permitting free rotation of the bone fixation element relative to the sleeve, and the exterior surface profile having at least a portion with a non-circular cross-section adapted to mate with the non-circular cross-section of the transverse opening, thereby preventing rotation of the sleeve with respect to the intramedullary pin; and
a locking mechanism configured and adapted to selectively lock rotation of the bone fixation element relative to the sleeve when in a first position and permit free rotation of the bone fixation element relative to the sleeve when in a second position.

2. The device of claim 1, wherein the bone fixation element, sliding sleeve and locking mechanism are adapted for insertion through the transverse opening in the pin as a single preassembled unit.

3. The device of claim 1, wherein the second end of the bone fixation element includes a longitudinal bore.

4. The device of claim 3, wherein the longitudinal bore at the second end of the bone fixation element is at least partially threaded.

5. The device of claim 4, wherein the locking mechanism is a fixing screw having a screw head with a diameter D and a screw shank with a diameter d having an outside thread, where D>d.

6. The device of claim 5, wherein the outside thread of the fixing screw shank corresponds to the threaded bore of the bone fixation element, and progressive tightening of the fixing screw within the threaded bore rotationally locks the bone fixation element with the sliding sleeve, thereby preventing rotation of the bone fixation element relative to the sliding sleeve.

7. The device of claim 1, wherein the bone fixation element is axially fixed relative to the sliding sleeve.

8. The device of claim 7, wherein the shaft of the bone fixation element includes a first annular groove and the internal surface profile of the sliding sleeve includes a second annular groove, and a ring element engages both the first and second annular grooves to prevent axial displacement of the shaft relative to the sliding sleeve.

9. The device of claim 1, wherein a rear end of the sliding sleeve extends a distance x past the second end of the bone fixation element, where x is at least 0.01 mm.

10. The device of claim 1, wherein the second end of the bone fixation element includes an externally threaded portion.

11. The device of claim 10, wherein the locking mechanism is a nut with an internal thread that corresponds to the externally threaded portion at the second end of the bone fixation element.

12. The device of claim 1, wherein the first end of the bone fixation element includes a helical blade.

13. The device of claim 12, wherein the helical blade has a pitch of at least 50 mm.

14. The device of claim 1, wherein the first end of the bone fixation element includes a screw thread, a chisel, a pin, a T-section or a double T-section.

15. The device of claim 1, wherein the first end of the bone fixation element includes a plurality of helical blades.

16. The device of claim 1, wherein the locking mechanism is adapted to limit axial displacement of the sliding sleeve relative to the intramedullary pin.

17. The device of claim 1, wherein the bone fixation element is a screw.

18. The device of claim 1, wherein the external surface profile of the sliding sleeve includes a longitudinal projection that mates with a longitudinal recess in the transverse opening.

19. A device for the treatment of femoral fractures comprising:
an intramedullary pin having a first longitudinal axis, a proximal portion, a distal portion, and at least one transverse opening through the proximal portion of the pin, the at least one transverse opening forming an oblique angle with the first longitudinal axis and having a non-circular cross-section;
a cross-member configured for insertion through the transverse opening to engage bone in the femoral head, the cross-member including:
a sliding sleeve having a central bore, a circular interior surface profile, and a non-circular exterior surface profile, the exterior surface profile adapted to mate with the non-circular cross-section of the transverse opening, thereby preventing rotation of the sleeve with respect to the intramedullary pin,
a bone fixation element having a first end, a second end, and a shaft, the first end configured and dimensioned to engage bone in the femoral head, and the shaft configured and dimensioned for free rotation within the central bore of the sliding sleeve, and a locking mechanism configured and adapted to selectively lock rotation of the bone fixing element relative to the sleeve when in a first position and permit free rotation of the bone fixing element relative to the sleeve when in a second position.

20. The device of claim 19, wherein the cross-member is adapted for insertion through the transverse opening in the pin as a single preassembled unit.

21. The device of claim 19, wherein the first end of the bone fixation element includes a helical blade.

22. The device of claim 19, wherein the bone fixation element is a screw.

* * * * *